(12) United States Patent
Carbonaro et al.

(10) Patent No.: US 9,128,139 B2
(45) Date of Patent: Sep. 8, 2015

(54) DIAGNOSIS METHOD AND CONTROL UNIT FOR PERFORMING A DIAGNOSIS OF A LAMBDA SENSOR OF THE UEGO TYPE OF AN EXHAUST SYSTEM FOR AN INTERNAL COMBUSTION ENGINE

(71) Applicant: Magneti Marelli S.p.A., Corbetta (IT)

(72) Inventors: Piero Maria Carbonaro, Turin (IT); Marco Ceroni, Turin (IT)

(73) Assignee: MAGNETI MARELLI S.P.A., Corbetta (IT)

( * ) Notice: Subject to any disclaimer, the term of this patent is extended or adjusted under 35 U.S.C. 154(b) by 233 days.

(21) Appl. No.: 13/687,141

(22) Filed: Nov. 28, 2012

(65) Prior Publication Data

US 2013/0234744 A1 Sep. 12, 2013

(30) Foreign Application Priority Data

Mar. 6, 2012 (IT) .............................. BO2012A0111

(51) Int. Cl.
  *G01R 31/00* (2006.01)
  *G01R 31/02* (2006.01)
  *G01N 27/417* (2006.01)
  *G01M 15/10* (2006.01)
  (Continued)

(52) U.S. Cl.
  CPC .......... *G01R 31/024* (2013.01); *F02D 41/1494* (2013.01); *F02D 41/1495* (2013.01); *G01M 15/104* (2013.01); *G01N 27/4175* (2013.01); *F02D 41/1456* (2013.01); *F02D 2041/2089* (2013.01); *F02D 2041/2093* (2013.01)

(58) Field of Classification Search
  CPC .......... G01R 31/2874; G01R 31/2866; G01R 31/2891
  USPC .......................................... 324/750.01, 750.3
  See application file for complete search history.

(56) References Cited

U.S. PATENT DOCUMENTS 5,616,835 A * 4/1997 Schnaibel et al. .......... 73/114.69
5,935,399 A * 8/1999 Tanaka et al. ................. 204/424
(Continued)

FOREIGN PATENT DOCUMENTS

DE         10049685 A1    4/2002
DE      102008031514 A1    4/2009
(Continued)

OTHER PUBLICATIONS

Dec. 18, 2012 Search Report for Italian Patent App. No. IT BO20120111.

*Primary Examiner* — Arleen M Vazquez
*Assistant Examiner* — Dominic Hawkins
(74) *Attorney, Agent, or Firm* — Howard & Howard Attorneys PLLC (57) ABSTRACT

A method performs a diagnosis of a lambda sensor of a "UEGO" type of an exhaust system for an internal-combustion engine. The lambda sensor includes a series of pins. The diagnosis method comprises steps of: heating the lambda sensor to cause the lambda sensor to reach an inner temperature that is higher than about 600° C.; polarizing a first one of the pins by connecting the first pin to a supply voltage through a first limiting resistance; measuring a voltage of all of the pins while the first pin is connected to the supply voltage; and diagnosing a presence of a short circuit to an electrical ground if the voltage of at least one of the pins is lower than a predetermined threshold. A control unit performs the diagnosis.

19 Claims, 9 Drawing Sheets

(51) Int. Cl.
*F02D 41/14* (2006.01)
*F02D 41/20* (2006.01)

(56) References Cited

U.S. PATENT DOCUMENTS

| | | | |
|---|---|---|---|
| 6,334,352 B1* | 1/2002 | Poggio et al. | 73/23.31 |
| 2002/0011097 A1* | 1/2002 | Kuderer et al. | 73/61.57 |
| 2002/0100698 A1* | 8/2002 | Detwiler et al. | 205/784.5 |
| 2004/0222094 A1* | 11/2004 | Ieda et al. | 204/424 |
| 2004/0238378 A1 | 12/2004 | Kumazawa et al. | |
| 2006/0157348 A1 | 7/2006 | Inoue et al. | |
| 2007/0125070 A1* | 6/2007 | Storhok et al. | 60/285 |
| 2010/0050605 A1* | 3/2010 | Thanasiu et al. | 60/286 |
| 2010/0123978 A1* | 5/2010 | Lin et al. | 361/18 |
| 2010/0200309 A1* | 8/2010 | Yilmaz et al. | 178/18.03 |
| 2012/0067033 A1* | 3/2012 | Leone et al. | 60/309 |
| 2012/0318045 A1* | 12/2012 | Aso et al. | 73/31.05 |
| 2013/0186169 A1* | 7/2013 | Bevot et al. | 73/1.06 |
| 2013/0234744 A1* | 9/2013 | Carbonaro et al. | 324/750.03 |

FOREIGN PATENT DOCUMENTS

| | | |
|---|---|---|
| EP | 1582726 A2 | 10/2005 |
| EP | 1707950 A2 | 10/2006 |

* cited by examiner

Fig. 9

DIAGNOSIS METHOD AND CONTROL UNIT FOR PERFORMING A DIAGNOSIS OF A LAMBDA SENSOR OF THE UEGO TYPE OF AN EXHAUST SYSTEM FOR AN INTERNAL COMBUSTION ENGINE

CROSS-REFERENCE TO RELATED APPLICATION

This application is based upon and claims priority to Italian Patent Application BO2012A 000111 filed on Mar. 6, 2012.

BACKGROUND OF INVENTION

1. Field of Invention

The invention relates to, in general, a diagnosis method and control unit for performing a diagnosis and, in particular, a diagnosis of a lambda sensor of the "UEGO" type of an exhaust system for an internal-combustion engine.

2. Description of Related Art

A lambda sensor of the "UEGO" (Universal Exhaust Gas Oxygen) type (also known as "linear oxygen sensor"), which provides a measurement of the oxygen content present in the exhaust gases, is used in an exhaust system for an internal-combustion engine.

The measurements provided by the lambda sensor of the "UEGO" type are used by the engine-control unit for adjusting the combustion in the cylinders of the internal-combustion engines to minimize the generation of polluting substances. It is, thus, apparent that if, following a fault, the lambda sensor of the "UEGO" type supplies incorrect measurements of the oxygen content present in the exhaust gases to the engine control, the engine control will incorrectly adjust the combustion in the cylinders of the internal-combustion engine, and, thus, an even very high increase of the generation of polluting substances will occur. Therefore, type-approval standards require to continuously diagnose the correct operation of the lambda sensor of the "UEGO" type to rapidly intervene with recovery strategies in case of malfunctioning of the lambda sensor of the "UEGO" type.

Currently, the known diagnosis of a lambda sensor of the "UEGO" type includes searching for the presence of a short circuit to a battery, the presence of a short circuit to ground, and the presence of an open (interrupted) circuit. However, the known diagnosis of a lambda sensor of the "UEGO" type allows the presence of a short circuit or of an open circuit to be identified, but does not allow to fully discriminate which type of fault is present and on which pin of the lambda sensor of the "UEGO" type the fault occurred.

SUMMARY OF INVENTION

The invention overcomes the disadvantages in the related art in a diagnosis method for performing a diagnosis of a lambda sensor of a "UEGO" type of an exhaust system for an internal-combustion engine. The lambda sensor includes a series of pins. The diagnosis method comprises steps of: heating the lambda sensor to cause the lambda sensor to reach an inner temperature that is higher than about 600° C.; polarizing a first one of the pins by connecting the first pin to a supply voltage through a first limiting resistance; measuring a voltage of all of the pins while the first pin is connected to the supply voltage; and diagnosing a presence of a short circuit to an electrical ground if the voltage of at least one of the pins is lower than a predetermined threshold.

The invention overcomes the disadvantages in the related art also in a control unit for performing the diagnosis. The control unit comprises a first switch that connects a first pin to a supply voltage through a first limiting resistance. A second switch connects the first pin to an electrical ground through a second limiting resistance. Each of a series of third switches connects each of the pins to the supply voltage through a third limiting resistance. Each of a series of fourth switches connects each of the pins to the electrical ground through a fourth limiting resistance. Each of a series of reading devices is permanently connected to a corresponding one of the pins and reads the voltage present in the pin.

It is the object of the invention to provide a diagnosis method and a control unit for performing a diagnosis of a lambda sensor of the "UEGO" type of an exhaust system for an internal-combustion engine, which diagnosis method and control unit are easy and cost-effective to be implemented while being free from the above-described drawbacks, thus allowing, in case of a single fault, to accurately identify the type of fault and the pin of the lambda sensor of the "UEGO" type on which the fault occurred.

According to the invention, a diagnosis method and a control unit for performing a diagnosis of a lambda sensor of the "UEGO" type of an exhaust system for an internal-combustion engine are provided.

Other objects, features, and advantages of the invention are readily appreciated as the invention becomes better understood while a subsequent detailed description of embodiments of the invention is read taken in conjunction with the accompanying drawing thereof.

BRIEF DESCRIPTION OF EACH FIGURE OF DRAWING OF INVENTION

DETAILED DESCRIPTION OF EMBODIMENTS OF INVENTION

Figure 1:
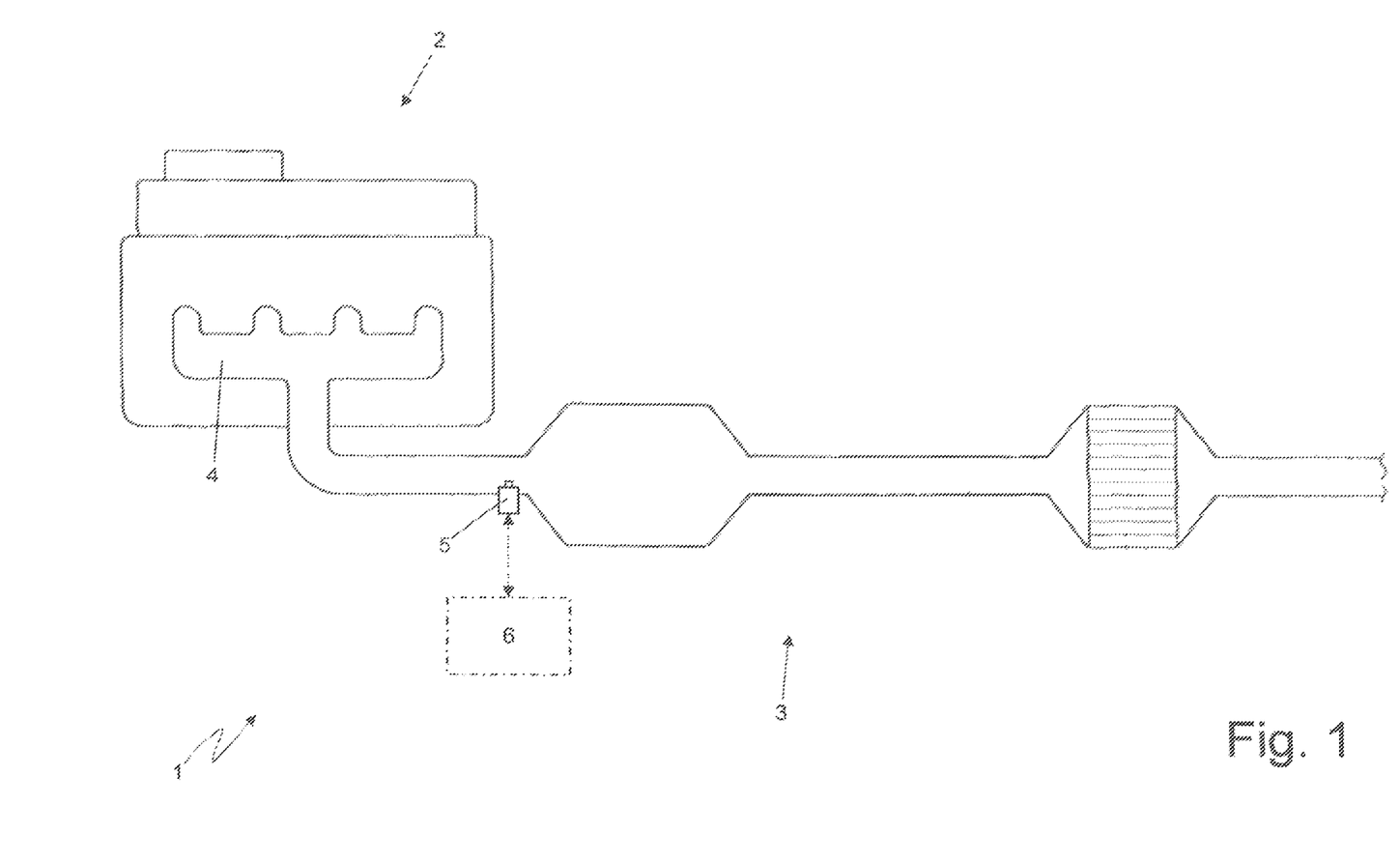
FIG. 1 is a diagrammatic view with parts removed for clarity of an exhaust system of an internal-combustion engine provided with a lambda sensor of the "UEGO" type that is diagnosed in accordance with the invention.

In FIG. 1, an exhaust system of an internal-combustion engine 2 is generally indicated at 1. The exhaust system 1 emits the gases produced by the combustion into the atmosphere and includes an exhaust pipe 3 that departs from an exhaust manifold 4 of the internal-combustion engine 2. A lambda sensor 5 of the "UEGO" type ("Universal Exhaust Gas Oxygen") (also known as "linear oxygen sensor") that measures the oxygen content in the exhaust gases is arranged along the exhaust pipe 3 and is connected to an electronic-control unit 6 ("ECU").

Figure 2:
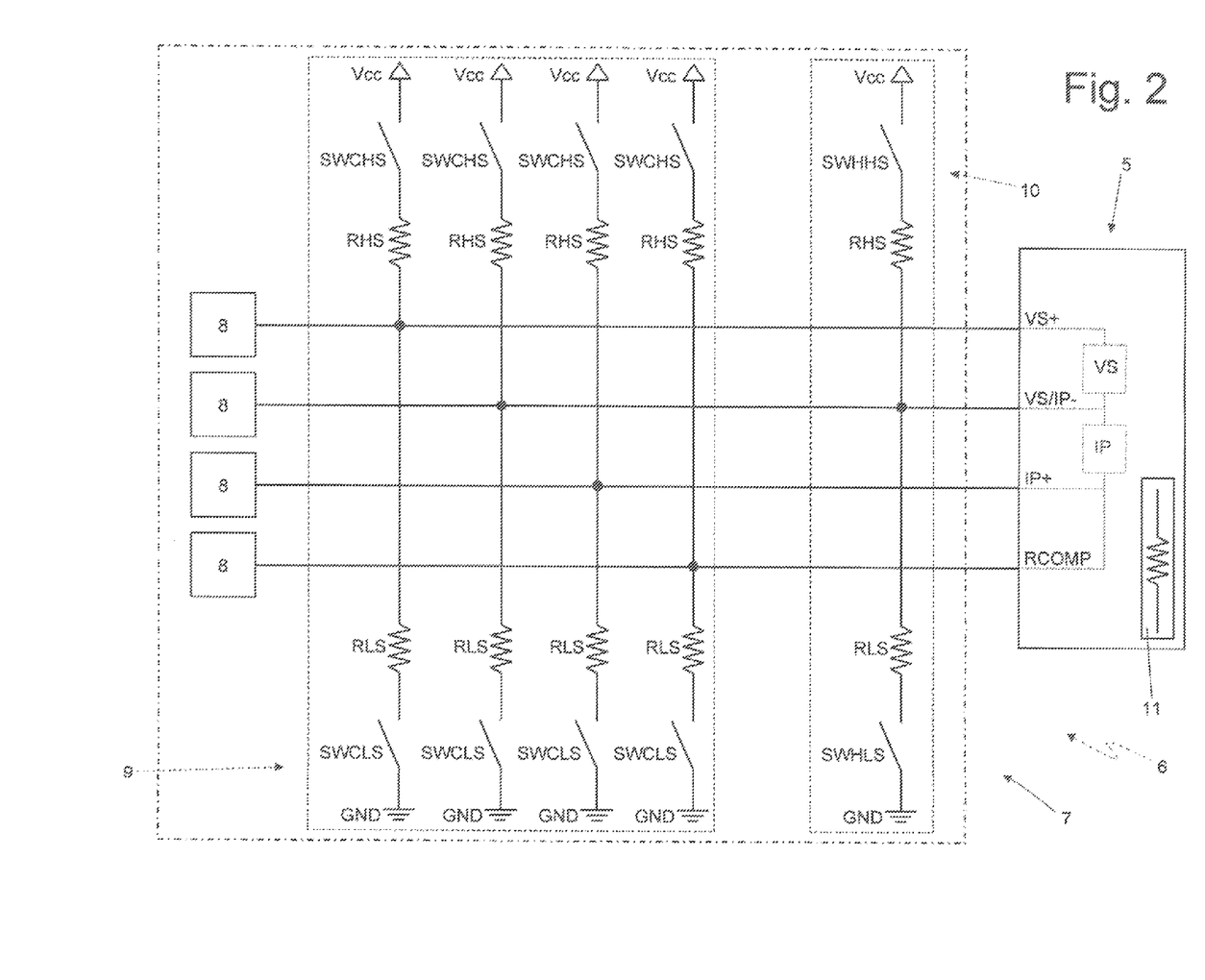
FIG. 2 is an electric diagram of the connections of the lambda sensor of the "UEGO" type in FIG. 1 for performing a diagnosis.

As shown in FIG. 2, the lambda sensor 5 of the "UEGO" type includes a pin VS+, a pin VS/IP−, a pin IP+, and a pin RCOMP, which are physically connected to the control unit 6 and are used by the control unit 6 to control the lambda sensor 5 of the "UEGO" type and, thus, to read the measurement of the oxygen content in the exhaust gases.

The pin RCOMP of the lambda sensor 5 of the "UEGO" type is connected to a compensation resistance integrated in the lambda sensor 5 of the "UEGO" type. In use, the control unit 6 measures the value of the compensation resistance through pin RCOMP and, therefore, establishes the correction entity that is applied to the measurements supplied by the lambda sensor 5 of the "UEGO" type as a function of the value of the compensation resistance.

Two Nernst cells VS, IP are integrated in the lambda sensor 5 of the "UEGO" type: Nernst cell VS is arranged between the exhaust gases and a reference cell and is electrically connected between pins VS+, VS/IP– whereas Nernst cell IP is arranged between the exhaust gases and the outside environment and is electrically connected between pins IP+, VS/IP–.

FIG. 2 diagrammatically shows a diagnosis circuit 7 that is integrated in the control unit 6 to diagnose the lambda sensor 5 of the "UEGO" type to search for the presence of a short circuit to a battery, the presence of a short circuit to ground, and the presence of an open (interrupted) circuit. The diagnosis circuit 7 includes four reading devices 8 each of which is permanently connected to a corresponding pin VS+, VS/IP–, IP+, RCOMP of the lambda sensor 5 of the "UEGO" type and is suited to read the voltage present in the pin VS+, VS/IP–, IP+, RCOMP. The diagnosis circuit 7 includes a "cold test" section 9 that, as described in detail below, applies the appropriate polarizations to pins VS+, VS/IP–, IP+, RCOMP of the lambda sensor 5 of the "UEGO" type when the lambda sensor 5 of the "UEGO" type is cold (i.e., has an inner temperature that is lower than 150-250° C.). The diagnosis circuit 7 includes a "hot test" section 10 that, as described in detail below, applies the appropriate polarizations to pin VS+, VS/IP of the lambda sensor 5 of the "UEGO" type when the lambda sensor 5 of the "UEGO" type is hot (i.e., has an inner temperature that is higher than 600-700° C.).

The "cold test" section 9 of the diagnosis circuit 7 includes a switch SWCHS (in practice, consisting of a transistor and of a decoupling diode integrated in the control unit 6) for each pin VS+, VS/IP–, IP+, RCOMP of the lambda sensor 5 of the "UEGO" type, which switch is suited to connect pin VS+, VS/IP–, IP+, RCOMP to the internal supply voltage Vcc (typically having a value of +5 volts) through a limiting resistance RHS (having a value of 10 kohms, for example). Furthermore, the "hot test" section 9 of the diagnosis circuit 7 includes a switch SWCLS (in practice, consisting of a transistor and of a decoupling diode integrated in the control unit 6) for each pin VS+, VS/IP–, IP+, RCOMP of the lambda sensor 5 of the "UEGO" type, which switch is suited to connect pin VS+, VS/IP–, IP+, RCOMP to the electric ground GND through a limiting resistance RHS (having a value of 10 kohms, for example).

The "hot test" section 10 of the diagnosis circuit 7 includes a switch SWHHS (in practice, consisting of a transistor and of a decoupling diode integrated in the control unit 6) for pin VS/IP– of the lambda sensor 5 of the "UEGO" type, which switch is suited to connect pin VS/IP– to the supply power Vcc through a limiting resistance RHS (having a value of 10 kohms, for example). Furthermore, the "hot test" section 10 of the diagnosis circuit 7 includes a switch SWHLS (in practice, consisting of a transistor and of a decoupling diode integrated in the control unit 6) for pin VS/IP– of the lambda sensor 5 of the "UEGO" type, which switch is suited to connect pin VS/IP– to the electric ground GND through a limiting resistance RLS (having a value of 10 kohms, for example).

The hot diagnosis of the lambda sensor 5 of the "UEGO" type (which is performed by using the "hot test" section 10 of the diagnosis circuit 7) allows to determine whether one of the pins VS+, VS/IP–, IP+, RCOMP of the lambda sensor 5 of the "UEGO" type is short circuited to the supply voltage Vcc or to the electric ground GND and allows to determine both whether one of the pins VS+, VS/IP–, IP+. RCOMP of the lambda sensor 5 of the "UEGO" type is disconnected (i.e., an open circuit is present) and which pin VS+, VS/IP–, IP+, RCOMP of the lambda sensor 5 of the "UEGO" type is possibly disconnected.

The hot diagnosis of the lambda sensor 5 of the "UEGO" type requires that the lambda sensor 5 of the "UEGO" type itself to be hot (i.e., have an inner temperature that is higher than 600-700° C.). For this purpose, a heater 11 of the lambda sensor 5 of the "UEGO" type [connected to the control unit 6 by two additional pins (not shown) of the lambda sensor 5 of the "UEGO" type] is controlled in an open-loop manner (i.e., without monitoring the temperature) by a duty-cycle that generates an electric power determined by a thermal model of the lambda sensor 5 of the "UEGO" type to take the inner temperature of the lambda sensor 5 of the "UEGO" type to exceed a temperature of approximately 600-700° C. When the inner temperature of the lambda sensor 5 of the "UEGO" type exceeds 600-700° C., pins VS+, VS/IP–, IP+, RCOMP are electrically connected to one another by internal resistances having a low value [of the order of a few tens of ohms (i.e., much lower than the polarization resistances RHS, RLS)]. Thus, if a given polarization voltage is applied to one of the pins VS+, VS/IP–, IP+, RCOMP in the absence of faults, the polarization voltage itself is transmitted substantially unchanged to the other pin VS+, VS/IP–, IP+, RCOMP.

Figure 3:
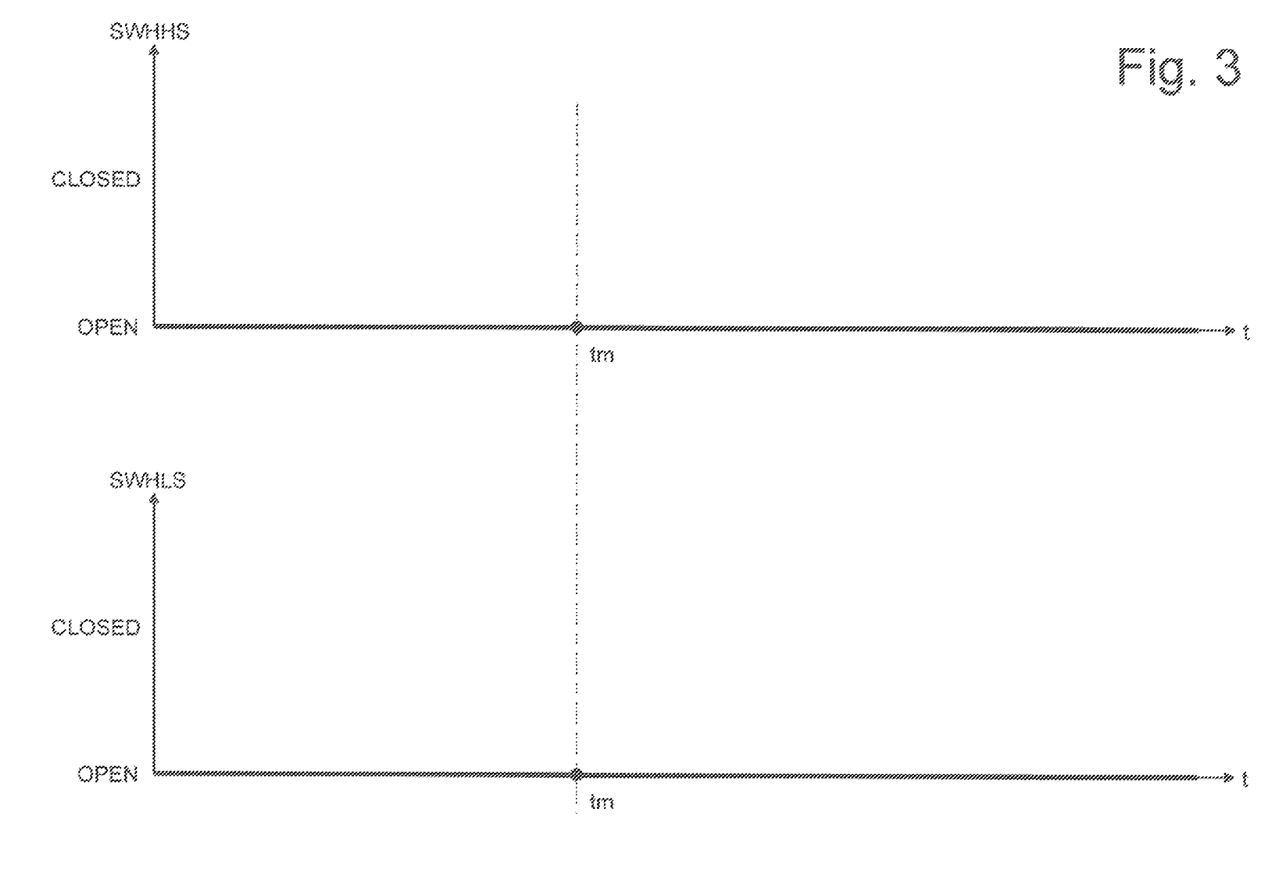
FIGS. 3-8 are time diagrams showing the driving modes for some switches of the wiring diagram in FIG. 2 while performing the diagnosis.

As shown in FIG. 3, the first part of the hot diagnosis of the lambda sensor 5 of the UEGO includes applying no type of polarization to pins VS+, VS/IP–, IP+, RCOMP keeping both switches SWHHS, SWHLS open. The voltages of the pins VS+, VS/IP–, IP+, RCOMP are measured by the reading devices 8 in a measuring instant tm. In the absence of faults, all pins VS-+, VS/IP–, IP+, RCOMP have a voltage close to zero (i.e., the voltage of electric ground GND), and, thus, the presence of a short circuit to a battery is diagnosed (without, however, being able to identify which pin VS+, VS/IP–, IP+, RCOMP is short circuited to a battery) if the pins VS+, VS/IP–, IP+, RCOMP have a voltage significantly different from zero (i.e., the voltage of electric ground GND). In other words, the presence of a short circuit to a battery is diagnosed if the voltage of at least one pin VS+, VS/IP–, IP+, RCOMP is higher than a predetermined threshold. The first part of the hot diagnosis of the lambda sensor 5 of the "UEGO" type does not subject the lambda sensor 5 of the "UEGO" type to any type of electric/thermal stress neither in the absence of faults nor in case of faults because no type of polarization is applied to pins VS+, VS/IP–, IP+, RCOMP.

The second part of the hot diagnosis of the lambda sensor 5 of the "UEGO" type is performed only if the result of first part of the hot diagnosis of the lambda sensor 5 of the "UEGO" type is negative (i.e., no presence of a short circuit to a battery was detected).

Figure 4:
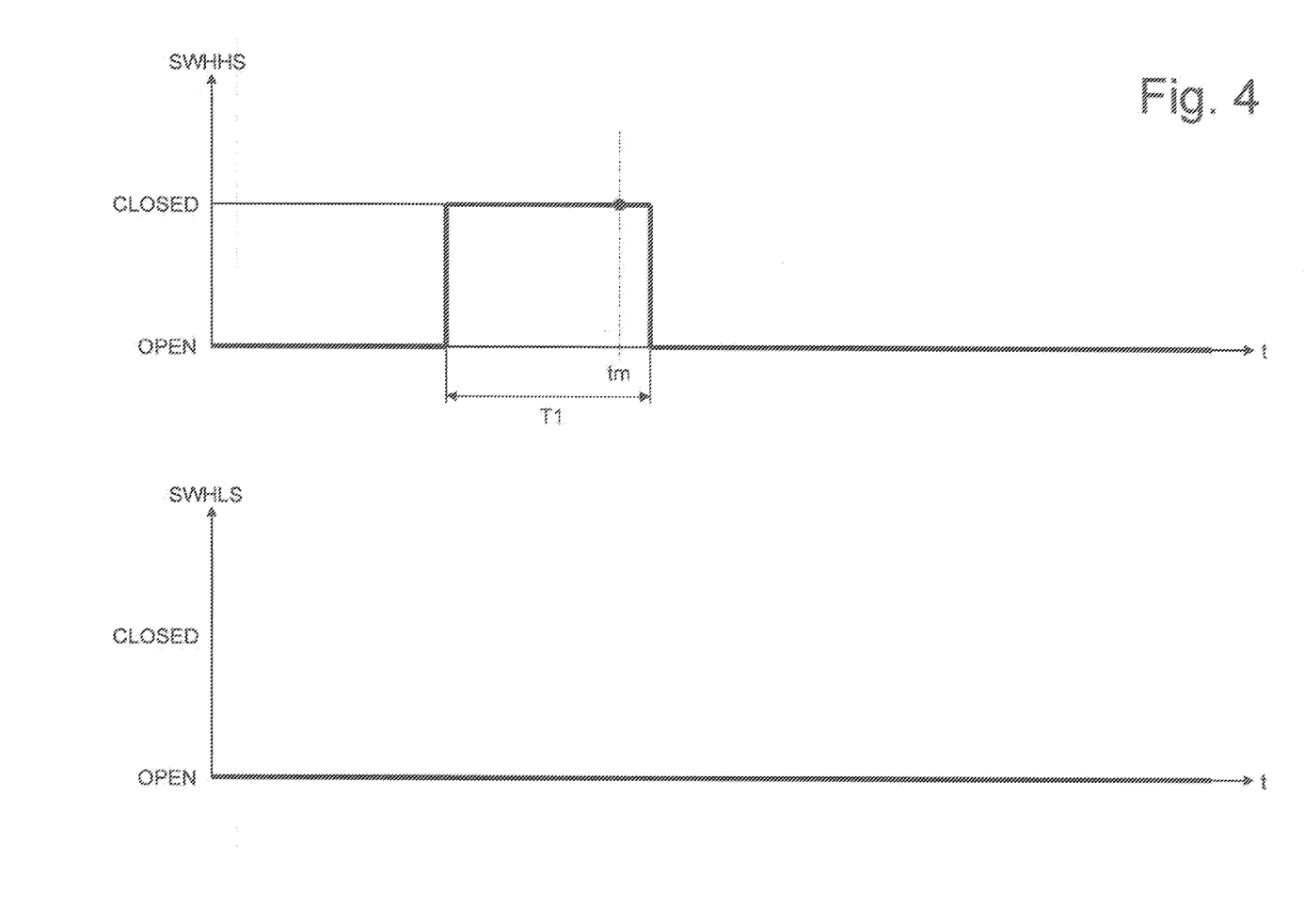

As shown in FIG. 4, the second part of the hot diagnosis of the lambda sensor 5 of the "UEGO" type includes connecting pin VS/IP– to supply voltage Vcc by closing the switch SWHHS (and obviously leaving the switch SWHLS open) for a time interval T1 (of the order of 8-16 msec). The voltages of the pins VS+, VS/IP–, IP+, RCOMP are measured in a measuring instant tm by the reading devices 8 (the measuring instant tm is set towards the end of the time interval T1 to allow the transient phenomena to end). In the absence of faults, all pins VS+, VS/IP–, IP+, RCOMP have a voltage substantially equal to supply voltage Vcc. Thus, if at least one of pins VS+, VS/IP–, IP+, RCOMP has a voltage close to zero (i.e., to the voltage of the electric ground GND), the presence of a short circuit to ground is diagnosed (without, however, being able to identify which pin VS+, VS/IP−, IP+, RCOMP is short circuited to ground). In other words, the presence of a short circuit to ground is diagnosed if the voltage of at least one pin VS+, VS/IP−, IP+, RCOMP is lower than a predetermined threshold.

Having excluded the presence of a short circuit to a battery by the first part of the hot diagnosis of the lambda sensor 5 of the "UEGO" type, in the absence of faults the second part of the hot diagnosis of the lambda sensor 5 of the "UEGO" type does not subject the lambda sensor 5 of the "UEGO" type to any type of electric/thermal stress. During the second part of the hot diagnosis of the lambda sensor 5 of the "UEGO" type, the presence of a short circuit to ground, and in the worst case, the maximum current that may cross the lambda sensor 5 of the "UEGO" type is equal to the supply voltage Vcc split by the limiting resistance RHS [i.e., of 0.45 mA (=4.5 V/10 kohms)]. A current (maximum) of 0.45 mA for the time interval T1 (of the order of 8-16 msec) is not a dangerous strain for the lambda sensor 5 of the "UEGO" type (i.e., cannot produce any destructive effects in the lambda sensor 5 of the "UEGO" type).

The third part of the hot diagnosis of the lambda sensor 5 of the "UEGO" type is performed only if the result of second part of the hot diagnosis of the lambda sensor 5 of the "UEGO" type is negative [i.e., no presence of a short circuit to ground was detected (the presence of a short circuit to a battery was already excluded at the end of the first part of the hot diagnosis of the lambda sensor 5 of the "UEGO" type)].

Figure 5:
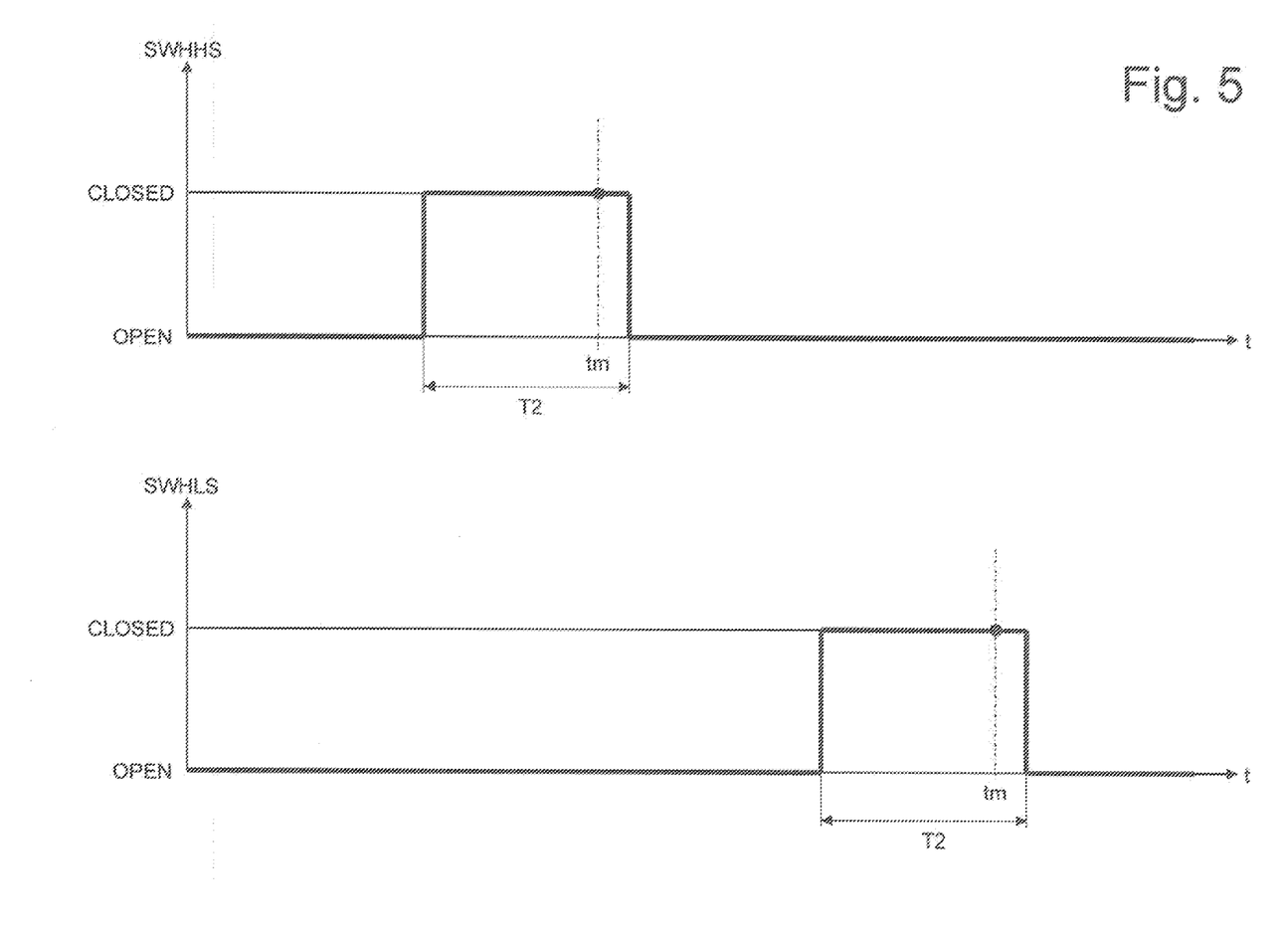

As shown in FIG. 5, the third part of the hot diagnosis of the lambda sensor 5 of the "UEGO" type includes connecting pin VS/IP− to the supply voltage Vcc closing switch SWHHS (and obviously leaving switch SWHLS open) for a time interval T2 (of the order of 0.5-2 sec) and in these conditions the voltage of the pins VS+, VS/IP−, IP+, RCOMP is measured by the reading devices 8 in a measuring instant tm (the measuring instant tm is set towards the end of the time interval T2 to allow the transient phenomena to end). Subsequently, and as shown in FIG. 5, the third part of the hot diagnosis of the lambda sensor 5 of the "UEGO" type includes connecting pin VS/IP− to the electric ground GND closing switch SWHLS (and obviously leaving switch SWHHS open) for a time interval T2 (of the order of 0.5-2 sec) and in these conditions the voltage of the pins VS+, VS/IP−, IP+, RCOMP is measured in a measuring instant tm by the reading devices 8 (the measuring instant tm is set towards the end of the time interval T2 to allow the transient phenomena to end).

A voltage difference ΔV is calculated for each pin VS+, VS/IP−, IP+, RCOMP that is equal to the difference between the voltage measured when pin VS/IP− was connected to the supply voltage Vcc through switch SWHHS and the voltage measured when pin VS/IP− was connected to the electric ground GND through switch SWHLS. In the absence of faults, the voltage difference ΔV is high (i.e., significantly different from zero and of the order of size of the supply voltage Vcc) for all pins VS+, VS/IP−, IP+, RCOMP, and, thus, disconnection of pin VS/IP is diagnosed (i.e., an open circuit is present at pin VS/IP−) if the voltage difference ΔV is high only for pin VS/IP−, and if the voltage difference ΔV is high for pin VS/IP− and for the other pins VS+, IP+, RCOMP except for one, then a disconnection of the pin in which the voltage difference ΔV is not high is diagnosed. In other words, the absence of open circuits is diagnosed if the voltage differences ΔV of all pins VS+, VS/IP−, IP+, RCOMP are higher than a predetermined threshold, a disconnection of pin VS/IP is diagnosed (i.e., an open circuit is present at pin VS/IP−) if the voltage difference ΔV of only pin VS/IP− is higher than the predetermined threshold, and finally a disconnection of the pin that has the voltage difference ΔV lower than the predetermined threshold is diagnosed if the voltage difference ΔV of only one pin VS+, IP+, RCOMP is lower than the predetermined threshold.

Having excluded the presence of a short circuit to a battery and of a short circuit to ground by the first part and second part of the hot diagnosis of the lambda sensor 5 of the "UEGO" type, the third part of the hot diagnosis of the lambda sensor 5 of the "UEGO" type does not subject the lambda sensor 5 of the "UEGO" type to any type of electric/thermal stress either in case of absence of faults or in the presence of an open circuit.

The cold diagnosis of the lambda sensor 5 of the "UEGO" type is performed after performing the hot diagnosis described above and only if the hot diagnosis has detected the presence of a short circuit to the supply voltage Vcc or to the electric ground GND and has the function of determining in which of the pins VS+, VS/IP−, IP+, RCOMP of the lambda sensor 5 of the "UEGO" type is the short circuit present.

Once the presence of a short circuit has been determined, the cold diagnosis of the lambda sensor 5 of the "UEGO" type (which is performed using the cold circuit section 9 of the diagnosis circuit 7) allows to determine which of the pins VS+, VS/IP−, IP−, RCOMP of the lambda sensor 5 of the "UEGO" type short circuited to the supply voltage Vcc or to the electric ground GND. The cold diagnosis of the lambda sensor 5 of the "UEGO" type requires the lambda sensor 5 of the "UEGO" type itself to be cold (i.e., to have an inner temperature that is lower than 150-250° C.). For this purpose, at the end of the hot diagnosis, the heater 11 of the lambda sensor 5 of the "UEGO" type is fully turned off and a sufficiently low time interval is waited to allow the natural cooling of the lambda sensor 5 of the "UEGO" type (possibly, it could be chosen to wait for the internal-combustion engine 2 to be turned off to run the cold diagnosis when the inner temperature of the lambda sensor 5 of the "UEGO" type is substantially equal to ambient temperature).

When the inner temperature of the lambda sensor 5 of the "UEGO" type is lower than a threshold temperature (indicatively of 150-250° C., pins VS+, VS/IP−, IP+, RCOMP are electrically connected to one another by high value internal resistances [of the order of a few tens of ohms (i.e., much lower than the value of the polarization resistances RHS and RLS)], and, thus, if a given polarization voltage is applied to one of the pins VS+, VS/IP−, IP+, RCOMP in the absence of faults, the polarization voltage itself is substantially not transmitted to the other pins VS+, VS/IP−, IP+, RCOMP.

Starting from the result of the previously performed hot diagnosis of the lambda sensor 5 of the "UEGO" type, if the cold diagnosis is performed a short circuit to the supply voltage Vcc or to the electric ground GND is necessarily present.

Figure 6:
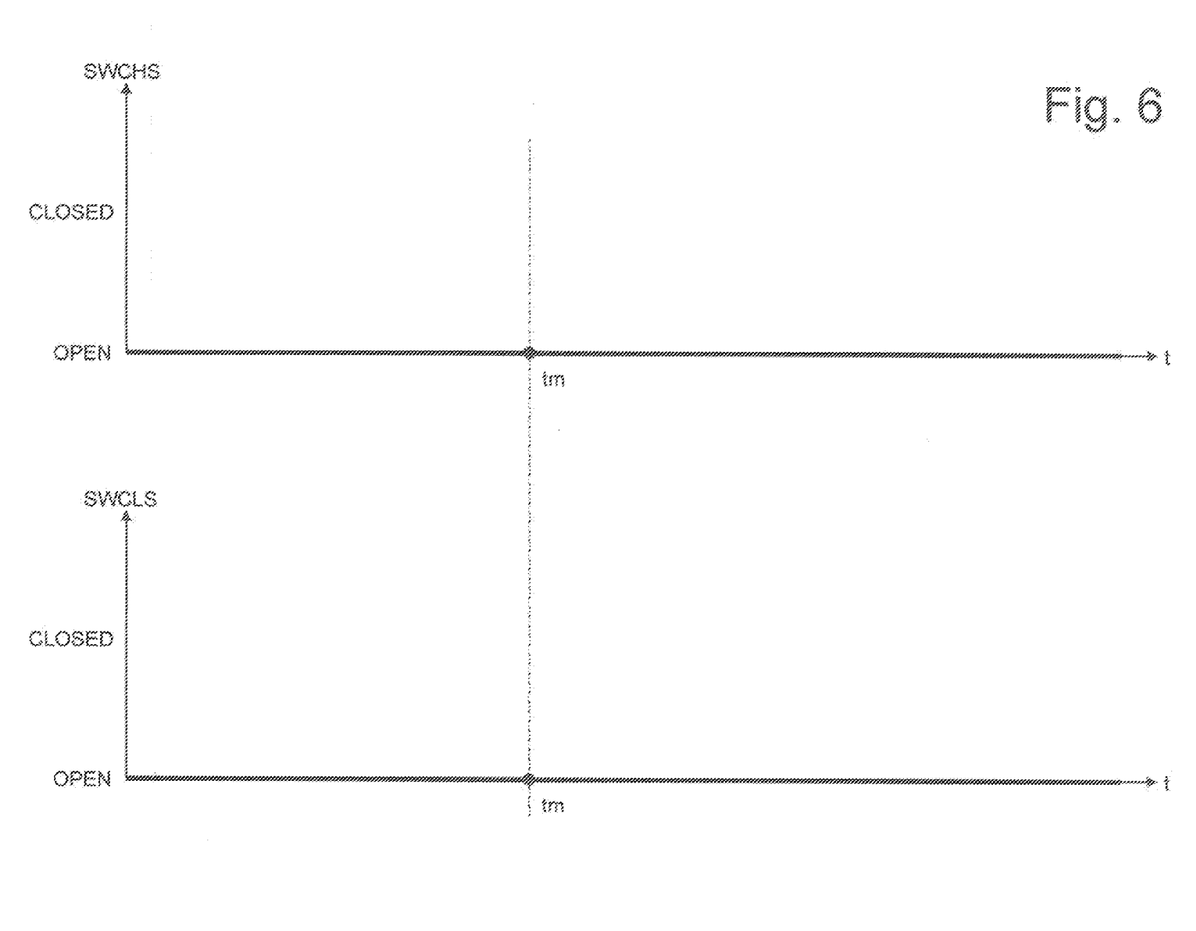

As shown in FIG. 6, the first part of the cold diagnosis of the lambda sensor 5 of the "UEGO" type includes not applying any type of polarization to pins VS+, VS/IP−, IP+, RCOMP maintaining both switches SWHHS, SWHLS open. The voltages of pins VS+, VS/IP−, IP+, RCOMP are measured by the reading devices 8 in a measuring instant tm. If all pins VS+, VS/IP−, IP+, RCOMP have a voltage close to zero (i.e., the voltage of the electric ground GND) then the presence of a short circuit to electric ground GND) is diagnosed, while if at least one pin VS+, VS/IP−, IP+, RCOMP has a voltage significantly different from zero (i.e., the voltage of the electric ground GND) then the presence of a short circuit to a battery is diagnosed. In other words, the presence of a short circuit to a battery is diagnosed if the voltage of at least one pin VS+, VS/IP−, IP+, RCOMP is higher than a predetermined threshold, otherwise the presence of a short circuit to electric ground GND is diagnosed if the voltage of all pins VS+, VS/IP−, IP+, RCOMP is lower than the predetermined threshold.

The first part of the cold diagnosis of the lambda sensor 5 of the "UEGO" type does not subject the lambda sensor 5 of the "UEGO" type to any type of electric/thermal stress because no type of polarization is applied to pins VS+, VS/IP−, IP+, RCOMP.

The first part of the cold diagnosis of the lambda sensor 5 of the "UEGO" type (which is identical to the first part of the hot diagnosis of the lambda sensor 5 of the "UEGO" type) may not be performed, because the hot diagnosis of the lambda sensor 5 of the "UEGO" type already provides information on the type of short circuit present (i.e., if a short circuit to the electric ground GND or a short circuit to a battery is present). In all cases, it is worth performing the first part of the cold diagnosis of the lambda sensor 5 of the "UEGO" type for the sake of caution (i.e., for additional, although redundant confirmation).

If and only if the first part of the cold diagnosis of the lambda sensor 5 of the "UEGO" type has determined the presence of a short circuit to the electric ground GND, then the second part of the cold diagnosis of the lambda sensor 5 of the "UEGO" type is performed to determine which pin VS+, VS/IP−, IP+, RCOMP is short circuited to electric ground GND. Instead, if and only if the first part of the cold diagnosis of the lambda sensor 5 of the "UEGO" type has determined the presence of a short circuit to a battery, then the third part of the cold diagnosis of the lambda sensor 5 of the "UEGO" type is performed to determine which pin VS+, VS/IP−, IP+, RCOMP is short circuited to a battery. Thus, the second and third part of the cold diagnosis of the lambda sensor 5 of the "UEGO" type are always mutually alternative.

Figure 7:
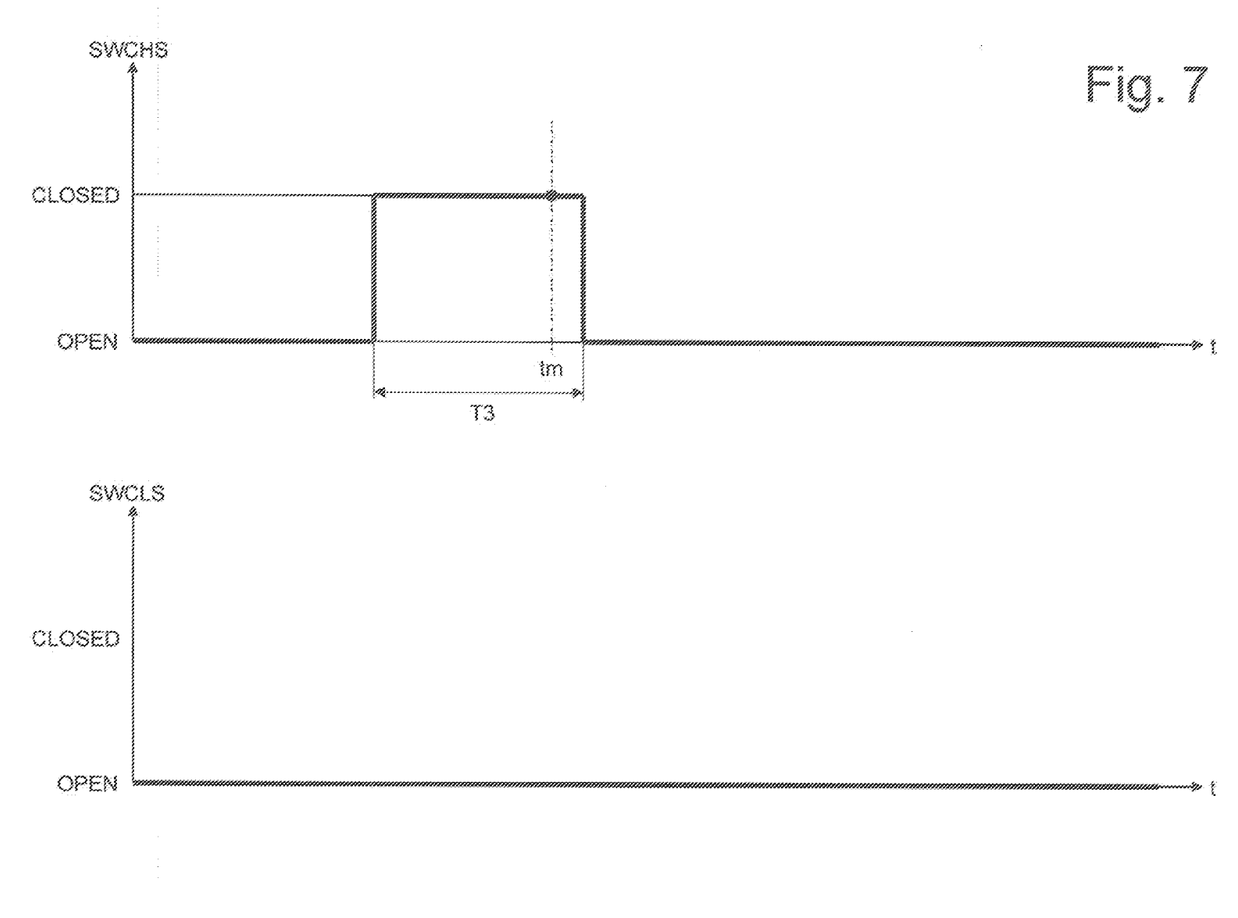

As shown in FIG. 7, the second part of the cold diagnosis of the lambda sensor 5 of the "UEGO" type includes connecting all pins VS+, VS/IP−, IP+, RCOMP to supply voltage Vcc by closing the switches SWCHS (and obviously leaving all the switches SWCLS open) for a time interval T3 (of the order of 3-10 msec). The voltages of the pins VS+, VS/IP−, IP+, RCOMP are measured in a measuring instant tm by the reading devices 8 (the measuring instant tm is set towards the end of the time interval T3 to allow the transient phenomena to end). Pins VS+, VS/IP−, IP−, RCOMP free from short circuit to the electric ground will have a voltage substantially equal to the supply voltage Vcc, while pin VS+, VS/IP−, IP+, RCOMP in which the electric ground GND is present will have a voltage close to zero (i.e., to the voltage of the electric ground GND). In other words, presence of a short circuit to the electric ground GND is diagnosed in the pin VS+, VS/IP−, IP+, RCOMP in which the voltage is lower than a predetermined threshold.

During the second part of the cold diagnosis of the lambda sensor 5 of the "UEGO" type, and in the worst case, the maximum current that may cross the lambda sensor 5 of the "UEGO" type is equal to the supply voltage Vcc split by the limiting resistance RHS [i.e., of 0.45 mA (=4.5 V/10 kohms)]. A current (maximum) of 0.45 mA for the time interval T1 (of the order of 3-10 msec) is not a dangerous strain for the lambda sensor 5 of the "UEGO" type (i.e., cannot produce any destructive effects in the lambda sensor 5 of the "UEGO" type).

Figure 8:
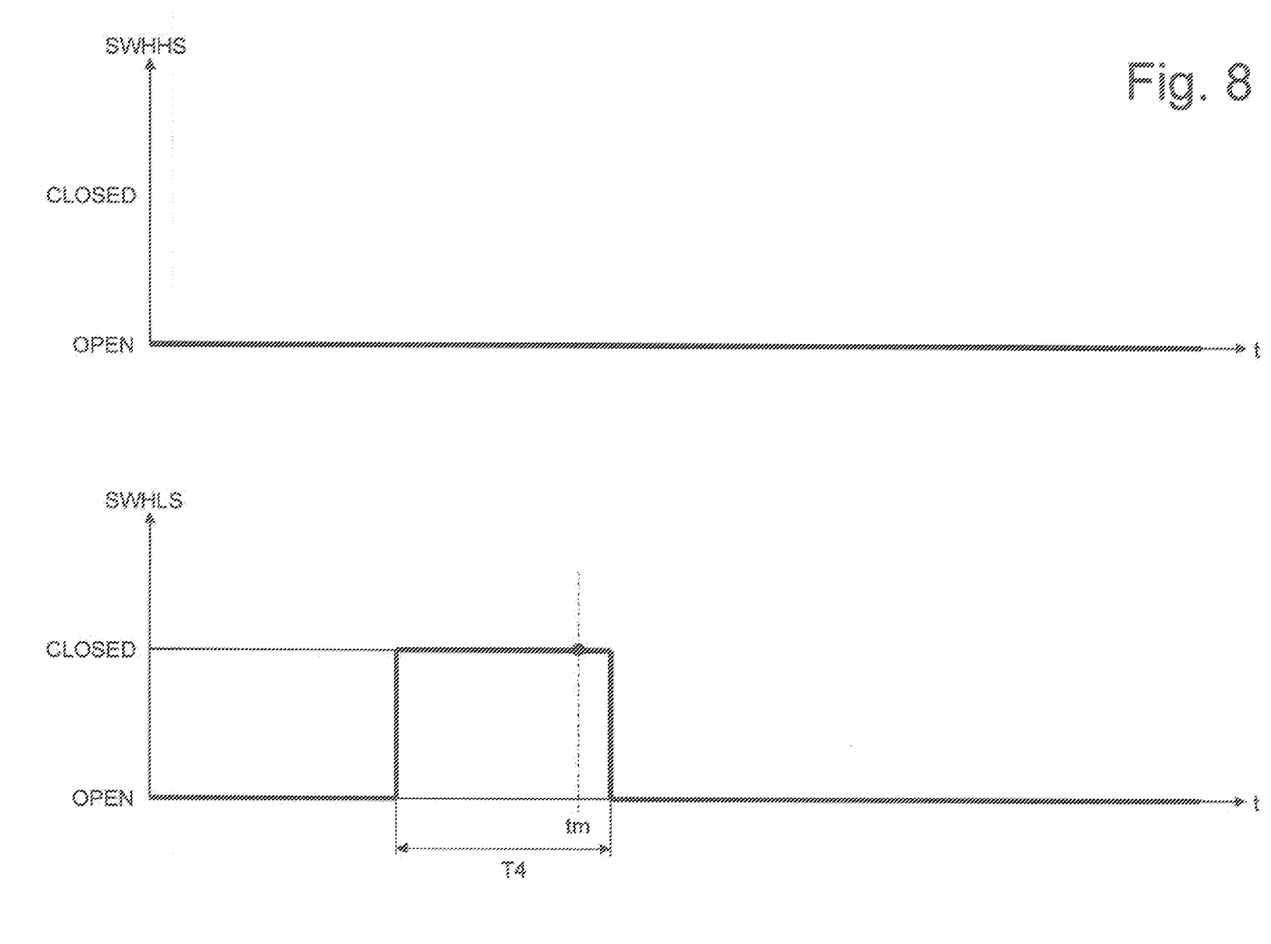
Figure 9:
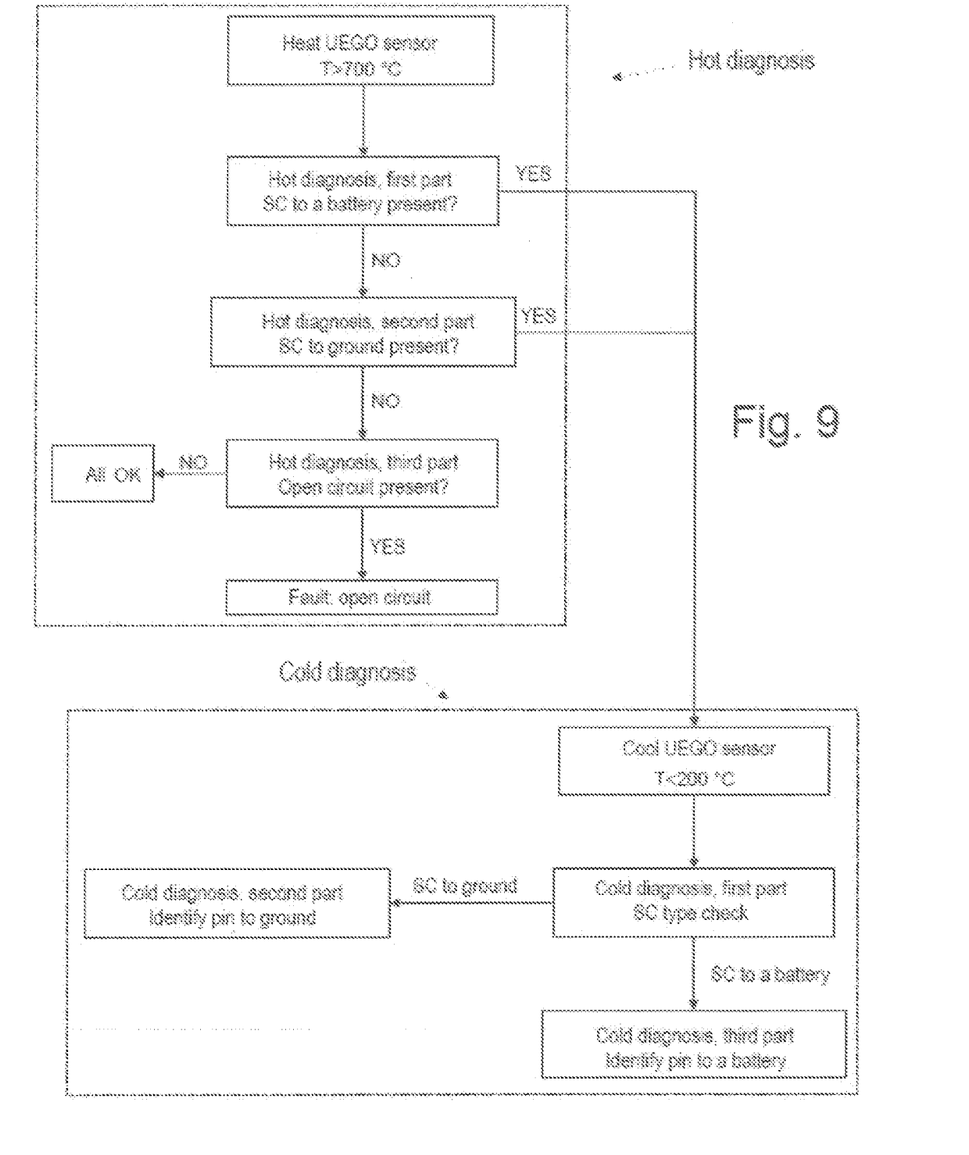
FIG. 9 is a block diagram that summarizes the various diagnosis steps.

As shown in FIG. 8, the third part of the cold diagnosis of the lambda sensor 5 of the "UEGO" type includes connecting all pins VS+, VS/IP−, IP−, RCOMP to the electric ground GND closing all the switches SWCLS (and obviously leaving all the switches SWCHS open) for a time interval T3 (of the order of 3-10 msec). The voltages of the pins VS+, VS/IP−, IP+, RCOMP are measured in a measuring instant tm by the reading devices 8 (the measuring instant tm is set towards the end of the time interval T3 to allow the transient phenomena to end). Pins VS+, VS/IP−, IP+, RCOMP free from short circuit to a battery will have a voltage close to zero (i.e., the voltage of the electric ground GND), while pin VS+, VS/IP−, IP+, RCOMP in which the electric ground GND is present will have a voltage substantially equal to the supply voltage Vcc. In other words, presence of a short circuit to a battery is diagnosed in the pin VS+, VS/IP−, IP+, RCOMP in which the voltage is higher than a predetermined threshold.

During the third part of the cold diagnosis of the lambda sensor 5 of the "UEGO" type, and in the worst case, the maximum current that may cross the lambda sensor 5 of the "UEGO" type is equal to the supply voltage Vcc split by the limiting resistance RHS [i.e., of 0.45 mA (=4.5 V/10 kohms)]. A (maximum) current of 0.45 mA for the time interval T3 (of the order of 3-10 msec) is not a dangerous strain for the lambda sensor 5 of the "UEGO" type (i.e., cannot produce any destructive effects in the lambda sensor 5 of the "UEGO" type).

It is worth noting that the value of the limiting resistances RHS and RLS is not random and is chosen as a function of the internal resistances between pins VS+, VS/IP−, IP+, RCOMP of the lambda sensor 5 of the "UEGO" type when the inner temperature of the lambda sensor 5 of the "UEGO" type is high (i.e., higher than 600-700° C.) and when the inner temperature of the lambda sensor 5 of the "UEGO" type is low (i.e., lower than 150-250° C.). Indeed, the limiting resistances RHS and RLS must be considerably larger (at least one order of size) than the internal resistances between the pins VS+, VS/IP−, IP+, RCOMP of the lambda sensor 5 of the "UEGO" type when the inner temperature of the lambda sensor 5 of the "UEGO" type is high (i.e., higher than 600-700° C.), and at the same time the limiting resistances RHS and RLS must be considerably smaller (at least one order of size) than the internal resistances between the pin VS+, VS/IP−, IP+, RCOMP of the lambda sensor 5 of the "UEGO" type when the inner temperature of the lambda sensor 5 of the "UEGO" type is low (i.e., lower than 150-250° C.). Indeed, only in this manner the presence of the resistances RHS and RLS will not negatively influence the diagnosis of the lambda sensor 5 of the "UEGO" type.

The above-described diagnosis method has many advantages. Firstly, the above-described diagnosis method allows to effectively and positively discriminate which type of fault is present and, above all, on which of the pins VS+, VS/IP−, IP+, RCOMP of the lambda sensor 5 of the "UEGO" type the fault occurred. In particular, the above-described diagnosis method allows to positively identify without errors possible faults present because the differences between the voltage measured by the measuring devices 8 and the corresponding comparison thresholds are always high and, therefore, always certain.

Furthermore, the above-described diagnosis method limits the injected current and the injection time in pins VS+, VS/IP−, IP+, RCOMP, avoiding the production of destructive effects in the lambda sensor 5 of the "UEGO" type.

Finally, the above-described diagnosis method is simple and cost-effective to be implemented as it requires neither high calculation/memory power nor particularly complex or non-standard hardware equipped with precision components.

The invention has been described above in an illustrative manner. It is to be understood that the terminology that has been used above is intended to be in the nature of words of description rather than of limitation. Many modifications and variations of the invention are possible in light of the above teachings. Therefore, within the scope of the appended claims, the invention may be practiced other than as specifically described above.

What is claimed is:

1. A diagnosis method for performing a diagnosis of a lambda sensor of a Universal Exhaust Gas Oxygen (UEGO) type of an exhaust system for an internal-combustion engine, wherein the lambda sensor includes a series of pins (VS+, VS/IP−, IP+, RCOMP) and the diagnosis method comprises steps of:
heating the lambda sensor to cause the lambda sensor to reach an inner temperature that is higher than about 600° C.;
polarizing a first one of the pins (VS/IP−) by connecting the first pin (VS/IP−) to a supply voltage (Vcc) through a first limiting resistance (RLS);
measuring a voltage of all of the pins (VS+, VS/IP−, IP+, RCOMP) while the first pin (VS/IP−) is connected to the supply voltage (Vcc); and
diagnosing a presence of a short circuit to an electrical ground (GND) if the voltage of at least one of the pins (VS+, VS/IP−, IP+, RCOMP) is lower than a predetermined threshold;
wherein the diagnosis method comprises further, after the diagnosis of the presence of the short circuit to the electrical ground (GND) is ended, steps of:
polarizing the first pin (VS/IP−) only by connecting the first pin (VS/IP−) to the supply voltage (Vcc) through the first limiting resistance (RLS);
measuring the voltage of all of the pins (VS+, VS/IP−, IP+, RCOMP) while the first pin (VS/IP−) is connected to the supply voltage (Vcc); polarizing the first pin (VS/IP−) only by connecting the first pin (VS/IP−) to the electrical ground (GND) through a second limiting resistance (RLS); measuring the voltage of all of the pins (VS+, VS/IP−, IP+, RCOMP) while the first pin (VS/IP−) is connected to the electrical ground (GND);
calculating, for each of pine (VS+, VS/IP−, IP+, RCOMP), a voltage difference (ΔV), which is equal to a difference between the voltage measured when the first pin (VS/IP−) was connected to the supply voltage (Vcc) and the voltage measured when the first pin (VS/IP−) was connected to the electrical ground (GND); and
diagnosing the presence of an open circuit if the voltage difference (ΔV) of at least one of the pins (VS+, VS/IP−, IP+, RCOMP) is lower than a predetermined threshold.

2. The diagnosis method according to claim 1, wherein the first pin (VS/IP−) is polarized by being connected to the supply voltage (Vcc) for a first time interval (T1) ranging from about 8 to about 16 msec.

3. The diagnosis method according to claim 1, wherein the diagnosis method comprises further, after the heating of the lambda sensor and before the polarization of the first pin (VS/IP), steps of:
polarizing none of the pins (VS+, VS/IP−, IP+, RCOMP) by keeping all of the pins (VS+, VS/IP−, IP+, RCOMP) insulated from the electrical ground (GND) and supply voltage (Vcc);
measuring the voltage of the pins (VS+, VS/IP−, IP+, RCOMP) while none of the pins (VS+, VS/IP−, IP+, RCOMP) is polarized; and
diagnosing the presence of a short circuit to the supply voltage (Vcc) if the voltage of at least one of the pins (VS+, VS/IP−, IP, RCOMP) is higher than a predetermined threshold.

4. The diagnosis method according to claim 3, wherein the first pin (VS/IP−) is polarized by connecting the first pin (VS/IP−) to the supply voltage (Vcc) only if the presence of a short circuit to the supply voltage (Vcc) has not been previously diagnosed.

5. The diagnosis method according to claim 1, wherein the diagnosis method comprises further steps of:
diagnosing the presence of an open circuit in the first pin (VS/IP−) if the voltage difference (6V) of all of the other pins (VS+, IP+, RCOMP) is lower than the predetermined threshold; and
diagnosing the presence of an open circuit in other of the pins (VS+, IP+, RCOMP) if the voltage difference (6V) of the first pin (VS/IP−) is higher than the predetermined threshold and the voltage difference (6V) of one of the other pins (VS+, IP+, RCOMP) is lower than the predetermined threshold.

6. The diagnosis method according to claim 1, wherein the first pin (VS/IP−) is polarized by being connected to the supply voltage (Vcc) and, subsequently, electrical ground (GND) for a second time interval (T2) ranging from about 0.5 to about 2 sec.

7. The diagnosis method according to claim 1, wherein the first pin (VS/IP−) is polarized by connecting the first pin (VS/IP−) to the supply voltage (Vcc) and electrical ground (GND) only if the presence of a short circuit to the electrical ground (GND) has not been previously diagnosed.

8. The diagnosis method according to claim 1, wherein the step of heating the lambda sensor involves controlling a heater of the lambda sensor in a substantially open-loop manner with an electric power that is determined by a thermal model of the lambda sensor.

9. The diagnosis method according to claim 1, wherein the diagnosis method comprises further, only if the presence of a short circuit to the electrical ground (GND) has been previously diagnosed, steps of:
letting the lambda sensor cool down as to cause the lambda sensor to reach an inner temperature that is lower than about 250° C.;
polarizing all of the pins (VS+, VS/IP−, IP+, RCOMP) by connecting all of the pins (VS+, VS/IP−, IP+, RCOMP) to the supply voltage (Vcc) through corresponding third limiting resistances (RHS);
measuring the voltage of all of the pins (VS+, VS/IP−, IP+, RCOMP) while all of the pins (VS+, VS/IP−, IP+, RCOMP) are connected to the supply voltage (Vcc); and
diagnosing the presence of a short circuit to the electrical ground (GND) in the pin (VS+, VS/IP−, IP+, RCOMP) in which the voltage is lower than a predetermined threshold.

10. The diagnosis method according to claim 1, wherein the diagnosis method comprises further, only if the presence of a short circuit to the supply voltage (Vcc) has been previously diagnosed, steps of:
letting the lambda sensor cool down, to cause the lambda sensor to reach an inner temperature that is lower than about 250° C.;
polarizing all of the pins (VS+, VS/IP−, IP+, RCOMP) by connecting all of the pins (VS+, VS/IP−, IP+, RCOMP) to the electrical ground (GND) through corresponding fourth limiting resistances (RLS);
measuring the voltage of all of the pins (VS+, VS/IP−, IP+, RCOMP) while all of the pins (VS+, VS/IP−, IP+, RCOMP) are connected to the electrical ground (GND); and diagnosing the presence of a short circuit to the supply voltage (Vcc) in the pin (VS+, VS/IP−, IP+, RCOMP) in which the voltage is higher than a predetermined threshold.

11. The diagnosis method according to claim 9, wherein the pins (VS+, VS/IP−, IP+, RCOMP) are polarized by being connected to either of the supply voltage (Vcc) and electrical ground (GND) for a third time interval (T3) ranging from about 8 to about 30 msec.

12. The diagnosis method according to claim 9, wherein the diagnosis method comprises further, after the cooling down of the lambda sensor and before the polarization of all of the pins (VS+, VS/IP−, IP+, RCOMP), steps of:
polarizing none of the pins (VS+, VS/IP−, IP+, RCOMP) by keeping all of the pins (VS+, VS/IP−, IP+, RCOMP) insulated from the electrical ground (GND) and supply voltage (Vcc); measuring the voltage of the pins (VS+, VS/IP−, IP+, RCOMP) while none of the pins (VS+, VS/IP−, IP+, RCOMP) is polarized;
diagnosing the presence of a short circuit to the supply voltage (Vcc) if the voltage of at least one of the pins (VS+, VS/IP−, IP+, RCOMP) is higher than a predetermined threshold; and
diagnosing the presence of a short circuit to the electrical ground (GND) if the voltage of all of the pins (VS+, VS/IP−, IP+, RCOMP) is lower than the predetermined threshold.

13. A control unit (6) for performing a diagnosis of a lambda sensor of Universal Exhaust Gas Oxygen (UEGO) type of an exhaust system for an internal-combustion engine, wherein the lambda sensor includes a series of pins (VS+, VS/IP−, IP+, RCOMP) and the control unit (6) comprises:
a first switch (SWHHS) that connects a first pin (VS/IP) to a supply voltage (Vcc) through a first limiting resistance (RHS);
a second switch (SWHLS) that connects the first pin (VS/IP) to an electrical ground (GND) through a second limiting resistance (RHS);
a series of third switches (SWCHS) each of which connects each of the pins (VS+, VS/IP−, IP+, RCOMP) to the supply voltage (Vcc) through a third limiting resistance (RHS);
a series of fourth switches (SWCHS) each of which connects each of the pins (VS+, VS/IP−, IP+, RCOMP) to the electrical ground (GND) through a fourth limiting resistance (RHS); and
a series of reading devices (8) each of which is permanently connected to a corresponding one of the pins (VS+, VS/IP−, IP++RCOMP) and reads the voltage present in the pin (VS+, VS/IP−, IP+RCOMP).

14. A diagnosis method for performing a diagnosis of a lambda sensor of a Universal Exhaust Gas Oxygen type of an exhaust system for an internal-combustion engine, wherein the lambda sensor includes a series of pins (VS+, VS/IP−, IP+, RCOMP) and the diagnosis method comprises steps of:
heating the lambda sensor to cause the lambda sensor to reach an inner temperature that is higher than about 600° C.;
polarizing a first one of the pins (VS/IP−) by connecting the first pin (VS/IP−) to a supply voltage (Vcc) through a first limiting resistance (RLS);
measuring a voltage of all of the pins (VS+, VS/IP−, IP+, RCOMP) while the first pin (VS/IP−) is connected to the supply voltage (Vcc); and diagnosing a presence of a short circuit to an electrical ground (GND) if the voltage of at least one of the pins (VS+, VS/IP−, IP+, RCOMP) is lower than a predetermined threshold;
wherein the diagnosis method comprises further, only if the presence of a short circuit to the electrical ground (GND) has been previously diagnosed, steps of:
letting the lambda sensor cool down as to cause the lambda sensor to reach an inner temperature that is lower than about 250° C.;
polarizing all of the pins (VS+, VS/IP−, IP+, RCOMP) by connecting all of the pins (VS+, VS/IP−, IP+, RCOMP) to the supply voltage (Vcc) through corresponding third limiting resistances (RHS);
measuring the voltage of all of the pins (VS+, VS/IP−, IP+, RCOMP) while all of the pins (VS+, VS/IP−, IP+, RCOMP) are connected to the supply voltage (Vcc); and
diagnosing the presence of a short circuit to the electrical ground (GND) in the pin (VS+, VS/IP−, IP+, RCOMP) in which the voltage is lower than a predetermined threshold.

15. The diagnosis method according to claim 14, wherein the pins (VS+, VS/IP−, IP+, RCOMP) are polarized by being connected to either of the supply voltage (Vcc) and electrical ground (GND) for a third time interval (T3) ranging from about 8 to about 30 msec.

16. The diagnosis method according to claim 14, wherein the diagnosis method comprises further, after the cooling down of the lambda sensor and before the polarization of all of the pins (VS+, VS/IP−, IP+, RCOMP), steps of:
polarizing none of the pins (VS+, VS/IP−, IP+, RCOMP) by keeping all of the pins (VS+, VS/IP−, IP+, RCOMP) insulated from the electrical ground (GND) and supply voltage (Vcc); measuring the voltage of the pins (VS+, VS/IP−, IP+, RCOMP) while none of the pins (VS+, VS/IP−, IP+, RCOMP) is polarized;
diagnosing the presence of a short circuit to the supply voltage (Vcc) if the voltage of at least one of the pins (VS+, VS/IP−, IP+, RCOMP) is higher than a predetermined threshold; and
diagnosing the presence of a short circuit to the electrical ground (GND) if the voltage of all of the pins (VS+, VS/IP−, IP+, RCOMP) is lower than the predetermined threshold.

17. A diagnosis method for performing a diagnosis of a lambda sensor of a Universal Exhaust Gas Oxygen type of an exhaust system for an internal-combustion engine, wherein the lambda sensor includes a series of pins (VS+, VS/IP−, IP+, RCOMP) and the diagnosis method comprises steps of:
heating the lambda sensor to cause the lambda sensor to reach an inner temperature that is higher than about 600° C.;
polarizing a first one of the pins (VS/IP−) by connecting the first pin (VS/IP−) to a supply voltage (Vcc) through a first limiting resistance (RLS);
measuring a voltage of all of the pins (VS+, VS/IP−, IP+, RCOMP) while the first pin (VS/IP−) is connected to the supply voltage (Vcc); and
diagnosing a presence of a short circuit to an electrical ground (GND) if the voltage of at least one of the pins (VS+, VS/IP−, IP+, RCOMP) is lower than a predetermined threshold;
wherein the diagnosis method comprises further, only if the presence of a short circuit to the supply voltage (Vcc) has been previously diagnosed, steps of:

letting the lambda sensor cool down, to cause the lambda sensor to reach an inner temperature that is lower than about 250° C.;

polarizing all of the pins (VS+, VS/IP−, IP+, RCOMP) by connecting all of the pins (VS+, VS/IP−, IP+, RCOMP) to the electrical ground (GND) through corresponding fourth limiting resistances (RLS);

measuring the voltage of all of the pins (VS+, VS/IP−, IP+, RCOMP) while all of the pins (VS+, VS/IP−, IP+, RCOMP) are connected to the electrical ground (GND); and diagnosing the presence of a short circuit to the supply voltage (Vcc) in the pin (VS+, VS/IP−, IP+, RCOMP) in which the voltage is higher than a predetermined threshold.

18. The diagnosis method according to claim 17, wherein the pins (VS+, VS/IP−, IP+, RCOMP) are polarized by being connected to either of the supply voltage (Vcc) and electrical ground (GND) for a third time interval (T3) ranging from about 8 to about 30 msec.

19. The diagnosis method according to claim 17, wherein the diagnosis method comprises further, after the cooling down of the lambda sensor and before the polarization of all of the pins (VS+, VS/IP−, IP+, RCOMP), steps of:

polarizing none of the pins (VS+, VS/IP−, IP+, RCOMP) by keeping all of the pins (VS+, VS/IP−, IP+, RCOMP) insulated from the electrical ground (GND) and supply voltage (Vcc); measuring the voltage of the pins (VS+, VS/IP−, IP+, RCOMP) while none of the pins (VS+, VS/IP−, IP+, RCOMP) is polarized;

diagnosing the presence of a short circuit to the supply voltage (Vcc) if the voltage of at least one of the pins (VS+, VS/IP−, IP+, RCOMP) is higher than a predetermined threshold; and diagnosing the presence of a short circuit to the electrical ground (GND) if the voltage of all of the pins (VS+, VS/IP−, IP+, RCOMP) is lower than the predetermined threshold.

\* \* \* \* \*